United States Patent [19]
Davidson

[11] Patent Number: 5,954,724
[45] Date of Patent: Sep. 21, 1999

[54] TITANIUM MOLYBDENUM HAFNIUM ALLOYS FOR MEDICAL IMPLANTS AND DEVICES

[76] Inventor: James A. Davidson, 615 Windsor Park La., Collierville, Tenn. 38017

[21] Appl. No.: 08/829,327

[22] Filed: Mar. 27, 1997

[51] Int. Cl.⁶ .................................................. C22C 14/00
[52] U.S. Cl. .............................. 606/76; 420/421; 148/421
[58] Field of Search .............................. 420/421; 606/76; 148/421

[56] References Cited

U.S. PATENT DOCUMENTS

| | | |
|---|---|---|
| 2,892,706 | 6/1959 | Jaffee et al. . |
| 2,948,607 | 8/1960 | Wagener . |
| 2,987,352 | 6/1961 | Watson . |
| 3,370,946 | 2/1968 | Bertea et al. . |
| 3,408,604 | 10/1968 | Doi et al. . |
| 3,643,658 | 2/1972 | Steinemenan . |
| 3,677,795 | 7/1972 | Bokros et al. . |
| 3,752,664 | 8/1973 | Steinemann . |
| 3,777,346 | 12/1973 | Steinemann . |
| 3,849,124 | 11/1974 | Villani . |
| 3,911,783 | 10/1975 | Gapp et al. . |
| 3,969,130 | 7/1976 | Bokrus . |
| 3,994,692 | 11/1976 | Rudy ....................................... 428/336 |
| 4,040,129 | 8/1977 | Steinemann et al. . |
| 4,145,764 | 3/1979 | Suzuki et al. . |
| 4,146,936 | 4/1979 | Aoyagi et al. . |
| 4,170,990 | 10/1979 | Baumgart et al. . |
| 4,197,643 | 4/1980 | Burstone et al. . |
| 4,278,630 | 7/1981 | Scheicher . |
| 4,511,411 | 4/1985 | Brunner et al. . |
| 4,668,290 | 5/1987 | Wang et al. . |
| 4,714,468 | 12/1987 | Wang et al. . |
| 4,769,041 | 9/1988 | Morscher . |
| 4,814,011 | 3/1989 | Kamohara et al. . |
| 4,857,269 | 8/1989 | Wang et al. . |
| 4,902,359 | 2/1990 | Takeuchi et al. . |
| 4,952,236 | 8/1990 | Wang et al. . |
| 4,983,184 | 1/1991 | Steinemann . |
| 5,169,597 | 12/1992 | Davidson et al. . |
| 5,232,361 | 8/1993 | Sachdeva et al. . |
| 5,415,704 | 5/1995 | Davidson ................................ 148/316 |
| 5,699,955 | 12/1997 | Shimizu .................................. 228/194 |

FOREIGN PATENT DOCUMENTS

| | | |
|---|---|---|
| 0437 079 A1 | 7/1991 | European Pat. Off. . |
| 513101 | 5/1976 | U.S.S.R. ................................. 420/421 |
| 1104942 | 3/1968 | United Kingdom ................... 420/421 |
| 1 297 152 | 11/1972 | United Kingdom ................... 420/421 |
| WO9638097 | 12/1996 | WIPO . |

OTHER PUBLICATIONS

Albert B. Ferguson, Jr., et al,; The Ionization of Metal Implants in Living Tissues; The Journal of Bone and Joint Surgery, Jan. 1960; pp. 77–90, page consisting of Fig. 1–Fig. 6.

D.C. Mears; Electron–Probe Microanalysis of Tissue and Cells from Implant Areas; The Journal of Bone and Joint Surgery; Aug. 1966; pp. 567–576.

T.P. Hoar, et al; Corrosion–Resistant Alloys in Chloride Solutions: Materials for Surgical Implants; pp. 486–510.

K.S. Jepson, et al; The Effect of Cooling Rate on the Beta Transformation in Titanium–Niobium and Titanium–Aluminum Alloys; pp. 677–690; Title Page to the Science, Technology and Application of Titanium.

Von Ulrich Zwicker, et al; Metallkundliche Probleme Und Supraleitung Bei Legierungen Auf Basis Titan–Niob, Die Als Werkstoffe für Die Herstellung Von Supraleitenden Magneten Dienen Können; Superconductivity and Metallurgical Problems with Titanium–Niobium Alloys Which May Serve as Materials for the Production of Superconducting Magnets; 1970—pp. 836–847.

W. Heller R. Löhberg; Einfluss Von Zusätzen Dritter Elemente Auf Das Kritische Magnetfeld Von Titan–Niob Legierungen; Journal of Less–Common Metals; Feb. 1971; pp. 265–276.

Von Helmut Albert, et al; Über Die Temperaturabhängigkeit Des Elastizitätsmoduls Von Niob–Titan–Legierungen; on the Temperature Dependence of Young's Modules of Niobium–Titanium Alloys; 1972; pp. 126–131.

Ein Jahrbuch, Herausgegeben Von Karl Schuchardt; Fortschritte Der Kieferund Gesichts–Chirurgie; pp. 49–56.

Charles J. Burstone and A. Jon Goldberg; Beta Titanium: A New Orthodontic Alloy; American Journal of Orthodontics; vol. 77, No. 2; Feb. 1980; pp. 121–132.

Donald Knittel; Titanium and Titanium Alloys; Kirk–Othmer Encyclopedia of Chemical Tech. vol. 23; 1983; pp. 98–113.

E.W. Collings; Sourcebook of Titanium Alloy Superconductivity; 1983; Chapter 10—p. 342; Chapter 11—pp. 352; 357; 358; 366.

E.W. Collings; Sourcebook of Titanium Alloy Superconductivity; Titanium–Niobium Base Quaternary Alloys, Chapter 13 pp. 405–412; pp. 418–419.

E.W. Collings; The Physical Metallurgy of Titanium Alloys; American Society for Metals, pp. 68–70.

E.W. Collings; The Physical Metallurgy of Titanium Alloys; Equilibrium Phases, pp. 39–48; Multicomponent Titanium––Base Alloys, p. 71; Nonequilibrium Phases, pp. 96–100.

E.W. Collings; The Physical Metallurgy of Titanium Alloys, pp. 40–41; Equilibrium Phases, pp. 66–69; Mechanical Properties: Elastic Properties, pp. 120–121; Aging: Microstructural Phenomenology, pp. 190–191, 194–195; References, pp. 214–215; 218–219; 226–227.

(List continued on next page.)

*Primary Examiner*—David H. Willse
*Attorney, Agent, or Firm*—Fulbright & Jaworski L.L.P.

[57] ABSTRACT

This invention describes a biocompatible, radiopaque, high-strength, low-modulus, titanium based alloy having about 2–30 weight percent Mo and up to about 30 weight percent Hf. This alloy is suitable for use in the fabrication of medical implants and devices having low modulus, improved corrosion resistance and surface hardening. To increase strength, Cr, Si and Fe can be added in small amounts as well as increasing levels of interstitial oxygen, nitrogen or carbon. To maintain low elastic modulus, Mo can be partially substituted by Nb.

20 Claims, 2 Drawing Sheets

OTHER PUBLICATIONS

Stanley A. Brown, D. Eng., and Katharine Merritt, Ph.D.; Evaluation of Corrosion Resistance of Biology; Feb. 13, 1986, pp. 1–3; Tables 1, 3, Figures 1, 2, 3.

R. Van Noort; Review—Titanium: The Implant Material of Today; Nov. 1987, pp. 3801–3811.

J.L. Murray; The Ti–Zr (Titanium–Zirconium) System; 1987, pp. 340–345.

J.L. Murray; The Nb–Ti (Niobium–Titanium) System; 1987, pp. 188–194.

Arthur J. Wilcock, Jr. on Orthodontic Wires; (JCO/Interviews), Aug. 1988; pp. 484–489.

The Japan Medical Review; vol. No. 12, Dec. 1991; Research and Development, pp. 12; 23.

William R. Proffit, D.D.S., Ph.D., et al; Contemporary Orthodontics; Chapter 10, Mechanical Principles in Orthodontic Force Control; pp. 289–315.

Anthony D. Viazis, DDS, MS; Atlas of Orthodontics; Principles and Clinical Applications; Chapter 6 Orthodontic Wires; pp. 153–162.

Daniel Eylon; Rodney R. Boyer, Donald A. Koss; Beta Titanium Alloys in the 1990's; Proceedings of a Symposium on Beta Titanium Alloys Sponsored by the Titanium Committee of TMS, held at the 1993 Annual TMS Meeting in Denver, CO, Feb. 22–24, 1993; Beta Titanium Alloys and Their Role in the Titanium Industry; Paul J. Bania; pp. 3–14.

Tiadyne™ 3510; Teledyne Wah Chang—2 pages.

TITANIUM MOLYBDENUM HAFNIUM ALLOYS FOR MEDICAL IMPLANTS AND DEVICES

FIELD OF THE INVENTION

The present invention relates to titanium alloys suitable for use in the construction of medical implants and devices and more particularly, a biocompatible, radiopaque, high-strength, low-modulus, high hardness titanium base alloy for medical implants and devices, having improved corrosion resistance due to the addition of hafnium and molybdenum and to additionally allow for surface hardening of an implant or device, made of this alloy.

BACKGROUND OF THE INVENTION

Alloy titanium has been used for all types of structures, including air craft, corrosion-resistant containers and medical implants. Titanium alloys are particularly useful for medical implants and other medical devices due to their excellent corrosion resistance and biocompatibility compared to alternative stainless steel and cobalt-chrome alloys in orthopaedic implants. Titanium and its alloys are more prone to fretting and wear compared to harder (Rc 42-44) Co—Cr—Mo alloys. The lower elastic modulus, in combination with high strength, however, allows titanium alloys to more closely approximate the stiffness of bone for use in orthopedic devices. Thus, devices formed from titanium alloys produce less bone stress shielding and consequently interfere less with bone viability. In orthodontic wire applications, a lower modulus of wire can provide a more gentle and uniform pressure over a larger displacement area than the stiffer stainless steel and cobalt alloys. Greater hardness can allow for less friction and improved motion. In cardiovascular implants, the lower stiffness of titanium alloys allows for a lower level of pressure exerted against soft tissue such as blood vessels, skin, various organ tissues and other soft tissue structures in the human body. Improved biocompatibility of titanium alloys and magnetic resonance imaging ability are additional advantages of titanium alloys.

Examples of titanium alloys used for medical devices include a low-modulus (less than 130 GPa) room temperature beta titanium alloy for orthopedic arch wire as described in U.S. Pat. No. 4,197,643. This patent describes the use of Mo, Nb, Ta and V to produce the beta alloy, and additionally, the use of Mn, Fe, Cr, Co, Ni, Cu, Al and Zr. There is no mention of the use of hafnium in the alloy. Alloy strength is achieved by aging to precipitate the alpha phase or by cold working. The preferred composition is Ti-11.5Mo-6Zi-4.5Sn, commonly called Beta III. However, the hardness is in the 30's on the Rockwell "C" scale. U.S. Pat. No. 5,312,247 describes a shape-memory or super elastic alloy having a predetermined activation temperature for use in orthopedic applications. This patent further describes the use of nickel-titanium based and titanium-molybdenum based alloys but as in the previous example, does not mention the use of hafnium (Hf) in the alloys. The use of nickel-containing metals is undesirable, not only in orthodontics, but in most medical device applications due to the common occurrence of nickel sensitivity of patients. The applicant is unaware of any Ti—Mo based alloys with shape memory properties, at least at temperatures useful in the human body. Nitinol is a commonly-used Ti—Ni alloy with shape memory behavior that is used in essentially all types of medical device applications. However, this highly elastic alloy is less than optimum with respect to other alternative available titanium alloys because the high concentrations of nickel interfere with the corrosion resistance properties of the alloys and the presence of the nickel sensitivity problem. Additionally, nickel can interfere with magnetic resonance imaging quality, and these alloys have a hardness in the Rc 30's. U.S. Pat. No. 5,232,361 describes an orthodontic bracket formulated of at least one of a group of alloys based on Ti, Zr, Si, B, Be, Cr, Nb and Co in a composition in which at least one of these elements exists in a range of between 40 weight percent and greater than 99 weight percent. An orthodontic bracket containing at least 45 weight percent titanium is given as an example. Other examples include alloys with at least 80 weight percent Ti with the addition of Al, V, Fe and/or Nb, and even a 99 weight percent Ti alloy. Once again, the use of hafnium is not described, and strength, elastic modulus, hardness, and biocompatibility are less than optimal.

Other examples of shape memory alloys include those described in U.S. Pat. Nos. 4,665,906 and 5,067,957 which describe medical devices and methods of installation using a non-specific shape memory alloy which displays stress induced martinsitic behavior, versus an activation temperature. The present inventive Ti alloy does not exhibit shape memory behavior, and contains hafnium to improve corrosion resistance and radiopacity. Additionally, unlike prior art Ti alloys described above, the presence of hafnium allows the option of surface hardening of the alloy via a conversion surface oxide, nitride, carbide, or combination of these.

Other titanium alloy device materials include those for orthopedic devices. For example, Ti-6Al-7Nb was developed several years ago to eliminate the potentially toxic effects of vanadium which is present in commonly used Ti-6Al-4V alloy (M. Semlitsch, Biomet. Technik, 1985). However, aluminum, which has been associated with Alzheimer and other neurological-related diseases, remains in this alloy. In view of this problem, others have proposed titanium alloy compositions with lower or no aluminum, or the absence of other toxic or carcinogenic elements associated with adverse responses to body function. As in the present inventive alloy, this aspect of biocompatibility has also been combined with an effort to reduce the elastic modulus of the titanium alloy, and to improve hardness over Ti-6Al-7Nb (Rc 34) and Ti-6Al-4V(Rc 34).

An early example of an improved titanium alloy for implants was discussed in U.S. Pat. No. 4,040,129 in which bone and dental implants having full tissue compatibility were described as being composed of a first component of about 3 to 30 weight percent selected from the group Nb, Ta, Cr, Mo and/or Al, and a second component of Ti and/or Zr; wherein the sum of the Cr, Mo and Al is less than 20 weight percent and the weights of Ti and/or Zr is less than 75 weight percent. This alloy was also free of Cu, Co, Ni, V and Sn. Examples described in the patent include Ti-9Nb-11Cr-3Al and Ti-4Mo-48Zr. However, the use of hafnium, surface hardenability, and radiopacity are not described.

Additionally, in U.S. Pat. No. 4,040,129, the benefit and desirability of a lower elastic modulus of the described alloy was not discussed but improved biocompatibility was. However, aluminum is found in the composition which, as mentioned above, has since been found to be associated with adverse neurological responses. No mention of the use of hafnium was given. A more recent patent, U.S. Pat. No. 4,857,269, also deals with the desirability of low elastic modulus in medical devices. This patent describes a titanium based alloy consisting of an amount of up to 24 weight percent of isomorphous beta stabilizers Mo, Ta, Nb and Zr, providing that molybdenum, when present, is at least 10 weight percent, and when present with zirconium, between 10 and 13 weight percent with the zirconium is being between 5 and 7 weight percent. Additionally, the same titanium based alloy also has up to 3 weight percent eutectoid beta stabilizers selected from Fe, Mn, Cr, Co and Ni, wherein the combined amount of isomorphous and eutectoid beta stabilizers is at least 1.2 weight percent. Optionally, up to 3 weight percent aluminum and lanthanum can be present in the alloy with the elastic modulus not exceeding 100 GPa (14.5 Msi). Examples include Ti-10-20Nb-1-4Zr-2Fe-0.5Al (TMZF)™. Once again, less than optimum elements (Mn, Co, Ni, Al), from a biocompatibility standpoint, are found in the alloy composition and there is no mention of hafnium or the ability to be surface hardened.

Various investigators in recent years have come to better understand the inherent biocompatibility of various elements. Laing, et al., in 1967, noted minor tissue reaction to implanted Ti, Zr, Nb, Ta and Ti alloys and a slightly greater reaction to pure, unalloyed Mo, V, Co, Ni, Mn and Fe. In another study in 1980, Steinemann concluded that vital elements Ti, Nb, Zr, Ta and Ti alloys, and Pt showed optimum biocompatibility and that the slightly less biocompatible elements included Al, Fe, Mo, Ag, Au and Co alloys and stainless steel. It was further noted that Co, Ni, Cu and V could be considered toxic. Hoars and Mears (1966) and Pourbaix (1984), based on electrochemical stability, suggested the use of Ti, Nb, Zr, and Ta as elemental constituents for improved biocompatibility. However, it is important to note that Ti—Mo alloys were included as acceptable materials and this was supported by comparative corrosion data between Ti and Ti-16Mo-3Nb-3Al in which the Ti—Mo alloy showed improved corrosion resistance. Thus, the presence of Mo in titanium alloys can actually be beneficial from the standpoint of corrosion and biocompatibility. It has also been reported in the titanium literature (*Titanium Alloys*, E. W. Collings, ASM, 1986) that the addition of more than about 4 weight percent molybdenum improved the corrosion resistance of titanium, particularly in crevice-type environments. With many of today's medical implants being modular in nature, this presents an issue not considered in the past. Further, to reduce fretting, corrosion and debris formation, increased hardness is desirable. The invention alloy is also designed to be greater than about 37 Rc. The above studies did not suggest the use of hafnium as a medical device metal or alloying addition. Hafnium is a sister element to zirconium and is more inert compared to zirconium.

In an effort to improve both the biocompatibility and to reduce elastic modulus in a titanium alloy, Davidson and Kovacs (U.S. Pat. No. 5,169,597) developed a medical implant titanium alloy with 10–20 weight percent Nb, or 30–50 weight percent Nb and 13–20 weight percent Zr, or sufficient Nb and/or Zr to act as a beta stabilizer by slowing transformation of beta (U.S. Pat. No. 5,545,227), where toxic elements are excluded from the alloy. The preferred example is Ti-13Nb-13Zr (Ti 1313™). Tantalum can also be used as a replacement for niobium where the sum of Nb and Ta is 10–20 weight percent of the alloy. Subsequent continuation-in-part patents and applications, describing this type of alloy for cardiovascular and dental implant devices, also exist and are considered herein with respect to prior art. All of these patents and applications describe the use of Ti, Nb, and/or Zr. However, the use of hafnium, molybdenum, the combination of Hf and Mo, or small quantities of selected strengthening elements is either not described or is specifically excluded. Further, the issue of hardness is not addressed, and the preferred composition (Ti-13Nb-13Zr) has a bulk hardness of only 33 Rc and even lower (Rc 24) in the quenched condition. Others, such as I. A. Okazaki, T. Tateishi and Y. Ito, have also proposed similar compositions including Ti-15Zr-4Nb-2Ta-0.2Pd and variations of the type Ti-5Zr-8Nb-2Ta-10-15-Zr-4-8-Nb-2-4Ta, Ti-10-20Sn-4-8Nb-2Ta-0.2Pd, and Ti-10-20 Zr-4-8Nb-0.2Pd. None however, addresses hardness, the inclusion of hafnium or the ability to be surface hardened.

Teledyne Wah Chang Albany, a major supplier of titanium, zirconium, niobium and their alloys, developed a Ti-35Nb-10Zr alloy. Due to the excellent biocompatibility of hafnium (1994 Teledyne Annual Report), Teledyne also developed titanium based alloys which include niobium and hafnium and a stiff, hard, Hf-based alloy as a replacement for Co—Cr—Mo bearing alloys. However, in the Teledyne annual report, no mention was given of molybdenum and its ability to reduce elastic modulus or the use of hafnium to improve corrosion resistance, nor its ability to be surface hardened. Neither was there any mention of incorporating hafnium with molybdenum in titanium alloys. This is due, most likely, to the general perception that molybdenum has less than optimum biocompatibility. However, as mentioned previously, other studies have shown that molybdenum, combined with titanium, can have excellent corrosion resistance and biocompatibility. Further, the presence of hafnium can improve radiopacity, which is important for small implants such as clips, stents and ear replacement components, as well as for endoscopic instruments used in cardiovascular and neurological devices. Similarly important is the fact that molybdenum can reduce the elastic modulus of the alloy.

Titanium alloys have a lower hardness than, for example, Co—Cr implant alloys and stainless steels. Due to this property, many investigators have studied and reported methods to harden titanium alloys, primarily through surface hardening processes. In addition to the improved bulk hardness of the inventive alloy, the inventive alloy is also designed to be surface hardened. The improved bulk hardness further improves the attachment strength of the surface coating formed, in part, from the presence of the hafnium in the composition of the inventive alloy. Prior art surface hardening methods include a wide range of overlay coating methods such as chemical and physical vapor deposition methods. These methods, however, require too high or too low a temperature, that results in metallurgical changes and less than optimum attachment of the hard, deposited, surface coating or require the use of an interlayer to improve attachment of the hard surface coating. Oxidation and nitriding methods can form a natural conversion surface oxide or nitride with a hard, built-in oxygen or oxygen rich, hardened metal interlayer. Examples of these are described in U.S. Pat. No. 5,372,660 for zirconium-containing titanium alloys, U.S. Pat. No. 5,037,438 for oxygen surface hardening of Zr and Zr—Nb alloys for implant bearing surfaces, and U.S. Pat. No. 5,152,794 for oxidation and nitriding of zirconium or zirconium alloy trauma devices with a surface layer 1–5 microns thick. Other similar patents exist for zirconium-containing titanium alloys and Zr—Nb alloys used in orthopedic and cardiovascular devices. See, for example, U.S. Pat. Nos. 5,282,852; 5,370,694 and 5,496,359. Internal oxidation is also described in U.S. Pat. No. 5,415,704, whereas U.S. Pat. No. 5,498,302 describes internal nitridization methods to harden a surface, but without the presence of a hard outer oxide or nitride layer.

Unlike oxygen or nitrogen diffusion methods which produce interstitial strengthening of the metal, internal oxidization or nitridization, using solute levels of more oxidizable or nitridable elements in quantities less than 2 weight percent, actually forms submicron oxide or nitride dispersions to produce the hardening. Other nitridizing processes to harden the surface are described in U.S. Pat. No. 5,419,984 for stainless steel, in U.S. Pat. No. 4,511,411 for titanium alloys using an autoclave containing nitrogen, and U.S. Pat. No. 5,334,264 which uses enhanced plasma nitriding methods. There are also studies of oxygen diffusion hardening of Ti, Ti-6Al-4V and Ti-6Nb-7V alloys (Streicher), and the use of N-ion implantation (Sioshanchi) which produces a much less effectively hardened and non-uniform surface. A wide variety of surface nitriding and oxidization options are available and known to those skilled in the art. In the non-medical literature, studies by Wallwork and Jenkins, 1959, exist on the oxidation of zirconium alloys, titanium alloys and hafnium showing the oxidation of hafnium producing a hard, well attached conversion surface oxide diffusion bonded to the metal substrate. However, these oxidation characteristics were obtained in an effort to reduce (resist) this process, and not to intentionally form the surface oxide to form a hard, protective, wear-resistant surface layer. Bania and Parris (Timet, Inc., Beta 215, Vol. II, 1990 Ti Conf.) investigated various Ti—Mo, Ti—Cr, Ti—Hf, Ti—Nb alloys and other alloys with respect to oxidation resistance that leads to the optimum composition of the beta 215 alloy (Ti-15Mo-2.8Nb-3Al). Specific combinations of Ti, Mo, and Hf were not investigated for implant applications or applications with optimal combinations of strength, hardness, and elastic modulus. Although not related to medical applications, nor related to reducing elastic modulus, radiopacity, or biocompatibility, Bania and Parris have shown that the addition of 15 weight percent molybdenum reduced the oxidation resistance of Ti-15Mo-5Zr versus pure Ti. Further, the addition of 5 weight percent Hf reduced oxidation resistance to a greater degree in Ti-15Mo-5Hf. An alloy of Ti-15Cr-5Mo and Ti-15Cr also showed substantially improved oxidation resistance versus a Ti or Ti-15Mo-5Zr alloy. The best oxidation resistance in this study was exhibited by Ti-15Mo-2-5Nb, and the addition of 3 weight percent Al further improved oxidation resistance, hence the development of Ti-21S. The use of this alloy, Ti-21S, has been proposed for medical implants (Bitambri and Shetty, 1994 Soc. Biomat. Pg. 195). However, the presence of Al in Ti-21S, along with only a marginal reduction in elastic modulus in the age-hardened condition, verses the elastic modulus of Ti-6Al-4V, renders this alloy less than optimum for medical implant applications. Thus, the above discussion illustrates the non-obviousness of the inventive Ti—Mo—Hf compositions as being useful for medical implant and device applications.

SUMMARY OF THE INVENTION

The present invention is a titanium based alloy suitable for use in the fabrication of medical implants and devices. The inventive alloy is a biocompatible, radiopaque, high-strength, low-modulus, high-hardness titanium based alloy having 2–30 weight percent Mo and up to about 30 weight percent Hf. Optionally, to further increase strength, Cr, Si and Fe can be added at levels less than about 3 weight percent. In addition, interstitial oxygen, nitrogen or carbon can be added for interstitial strengthening. To reduce or maintain the relatively lower elastic modulus of the alloy, Mo can be partially substituted by Nb. Medical implants and devices manufactured from these alloys have improved corrosion resistance, fretting resistance, and the ability to be surface hardened. The inventive alloy, with its unique combination of corrosion resistance, strength, modulus, and bulk hardness may be additionally suitable for non-medical device applications such as cable, springs, structural aeronautic components, oil field equipment, chemical processing, marine devices, fasteners, valves, and other applications.

BRIEF DESCRIPTION OF THE DRAWINGS

The invention will become more apparent when the detailed description of exemplary embodiments is considered in conjunction with the appended drawings, in which.

DETAILED DESCRIPTION OF PREFERRED EMBODIMENTS

The inventive alloy can be produced by combining as commercially pure components, titanium, molybdenum and hafnium in the appropriate proportions. The method for titanium alloy production, such as casting, powder metallurgy, etc. are well known to those of ordinary skill in the art of metallurgy and the production of the alloy requires no special skills or precautions beyond the materials, proportions and techniques described below.

The present invention comprises a biocompatible, radiopaque, high-strength, low-modulus, high-hardness titanium base alloy for the manufacture of medical implants and devices having improved corrosion resistance due to the combined addition of 2–30 weight percent molybdenum (Mo) and up to about 30 weight percent hafnium (Hf) which additionally allows for the surface hardening of a medical implant or device manufactured from the inventive alloy. If desired, the amount of molybdenum can be adjusted such that the elastic modulus of the alloy is minimized. In one preferred embodiment, the titanium alloy composition is titanium, 7 weight percent Mo and 7 weight percent Hf which has an as-quenched modulus of 12 msi (vs 16.5 for Ti-6Al-4V) and an aged strength of 190 Ksi (vs. 173 Ksi for TMZF™ and only 145 Ksi for Ti1313™). Substitution of molybdenum with niobium is also incorporated within the scope of the invention, wherein niobium partially substitutes for the molybdenum in the alloy. In two preferred embodiments the titanium alloy composition is titanium, 6 weight percent Mo, 15 weight percent Nb, and 6 weight percent Hf and another is titanium, 2 weight percent molybdenum, weight percent niobium and 6 weight percent hafnium.

The inventive alloy can be quenched from the above reduced beta transus (reduced to less than about 830° C. by the presence of Mo and Hf) to form a martensite that can be easily cold or warm worked and can respond to age hardening. Such cold- or warm-working of the invention alloy can also increase strength and reduce the elastic modulus, and is known by those skilled in the art. The amount of hafnium added to the alloy is of an amount sufficient to assist with the stabilization of the beta phase via lowering of the beta transus to improve strength and bulk hardness, improve corrosion resistance, provide improved radiopacity, and to form a hard, abrasion-resistant conversion surface oxide or nitride through standard oxidation and nitridization methods, known by those skilled in the art. The presence of a hard, inert, abrasion resistant ceramic surface layer in the inventive alloy, particularly in combination with improved bulk hardness, presents an important option for medical implants and devices in which it is desirable to have lower friction and wear, improved cutting ability, electrical insulation, and improved corrosion resistance. This improved oxidation resistance of the inventive alloy is a reflection of the ability of hafnium to more readily oxidize and control the surface layer properties than zirconium and thus, lower the potential for hydrogen to diffuse into the alloy, if hydrogen is present during a conversion hardening process. Hydrogen can be detrimental to titanium alloys by the potential formation of hydrides formed during the conversion hardening process. Typical conversion hardening temperatures for the inventive alloy include a range from between about 300 to 700° C. for oxidation and from a range between about 700 to 1100° C. for nitridization. The time at temperature can be varied depending on the desired amount of oxide or nitride on the surface.

Various properties of hafnium, titanium and molybdenum are given in Table I in comparison to other group 4, 5, 6 and 8 transition metals. These elements represent the majority of constituents considered for various titanium alloy medical devices, such as Nb, Zr, Ta, V and Fe.

Table I shows that the valence, atomic radius and crystal structure of hafnium is very comparable of that of zirconium. As mentioned previously, it is often referred to as the sister element of zirconium. However, the free energy of formation of the oxide is greater for hafnium than for zirconium, which should result in improved surface hardening and corrosion resistance. The atomic weight of hafnium is about twice that of zirconium which improves radiopacity. Hafnium, being further away from titanium in the periodic table than zirconium, should improve substitutional solid solution strengthening and bulk hardening. The magnetic susceptibility of hafnium is also lower than zirconium, which improves the magnetic residence imaging (MRI) response of the implant or device manufactured from the inventive alloy. Further, under oxidation and nitriding, hafnium will produce oxide or nitride attachment strength and abrasion resistance comparable to zirconium due to the similar ratios of oxide to metal volumes. However, with improved bulk hardness of the inventive alloy, the surface oxide or nitride can be expected to have improved abrasion resistance due to a lower stress concentration between the surface layer and metal substrate. In addition, the alloy can be hot or cold mechanically worked to optimize grain size, strength, elastic modulus, and toughness. Cold working in the softer, lower-modulus as-quenched condition can further reduce modulus as well as increase strength.

The addition of niobium to a titanium alloy can reduce the elastic modulus of the alloy with a minimum at about 16 weight percent Nb. However, the presence of molybdenum in a titanium alloy can also reduce the elastic modulus with a minimum at about 6 weight percent Mo as well as improve corrosion resistance of an implant manufactured from the inventive alloy, particularly in reducing-type, low pH environments, such as those created by passive oxide film damage in crevices in modular implants. Zirconium can improve corrosion resistance, however, hafnium improves corrosion resistance in the alloy to a greater degree in oxidizing high pH environments. This phenomenon is well described by Pourbaix. Although niobium and zirconium in a titanium alloy can be beneficial with respect to medical devices, the novel combination of molybdenum and hafnium can be expected to provide even greater benefits in a titanium alloy.

Metallurgically, zirconium can provide marginal strengthening of titanium alloys, but hafnium can provide slightly more strengthening and improved bulk hardening. Both

TABLE I

Selected Transition Elements and Their Properties

| ELEMENT (Group No.) | Ti (4) | Zr (4) | Hf (4) | V (5) | Nb (5) | Ta (5) | Cr (6) | Mo (6) | Fe (6) |
|---|---|---|---|---|---|---|---|---|---|
| Atomic No. | 22 | 40 | 72 | 23 | 41 | 73 | 24 | 42 | 26 |
| Crystal Structure | HCP | HCP | HCP | BCC | BCC | BCC | BCC | BCC | BCC |
| Atomic Radius (Å) | 1.458 | 1.58 | 1.59 | 1.32 | 1.43 | 1.43 | 1.25 | 1.36 | 1.24 |
| Melt Temp (°C.) | 1670 | 1855 | 2231 | 1910 | 2469 | 3020 | 1890 | 2625 | 1539 |
| Atomic Weight | 47.90 | 91.22 | 178.5 | 50.94 | 92.91 | 180.95 | 52.00 | 95.94 | 55.85 |
| Density (g/cm$^3$) | 4.54 | 6.5 | 11.4 | 6.0 | 8.57 | 16.6 | 7.19 | 10.2 | 7.87 |
| Elastic Modulus (GPa) | 107 | 100 | 137 | 138 | 103 | 186 | 289 | 324 | 200 |
| Tensile Str. (MPa) | 24 | 289 | 445 | 496 | NA | 414 | NA | 655 | NA |
| -ΔG(oxide) K Cal. | 280 | 300 | 334 | 137 | 120 | 644 | 323 | 180 | 63 |
| -ΔG(nitride) K Cal. | 160 | 195 | 165 | 130 | 114 | 119 | 52 | 34 | 2 |
| Valence (common) | 4 | 4 | 4 | 3,5 | 5 | 5 | 3 | 4,6 | 2,3 |
| Ratio: Vol. Ox/Vol. metal | 1.76 | 1.57 | 1.62 | 1.85 | 2.74 | 2.47 | 2.02 | 3.27 | 2.20 |
| Mag. Susceptibility $10^{-6}$ ergs | 153 | 122 | 75 | 255 | 195 | 154 | 180 | 89 | >15,000 (mag.) | stabilize the alpha and beta phase, and thus lower the beta transus via a more sluggish transformation. However, niobium is a weaker beta stabilizer than molybdenum. Formability of an alloy improves if the beta transus can be lowered such that a martensitic transformation occurs following rapid cooling or quenching. In this regard molybdenum is more effective than niobium. This martensitic structure can also allow the alloy to be aged hardened which can occur simultaneously with formation of a hard conversion oxide or nitride surface. An amount of about a 13 weight percent of niobium is required to produce a martensitic start (Ms) temperature of 600 degrees C., while only 6 weight percent of molybdenum is required. Further, molybdenum provides almost twice the strengthening and hardening of titanium as compared to niobium. In a titanium alloy including molybdenum above about 11 weight percent, transformation-aided ductility can also result. Orthorhombic (alpha double prime) martensite can result during quenching of a titanium alloy that includes molybdenum above about a 4 weight percent. However, more than 10 weight percent niobium is required, or 26 weight percent tantalum, to accomplish the same response in a titanium alloy. In a titanium alloy, molybdenum greater than about 6 weight percent is required in order to minimize or eliminate any untransformed beta. The beta transus for this level of molybdenum (6 weight percent) is less than about 850° C., and upon quenching, a fine dispersion of hexagonal omega phase precipitates can result. The addition of zirconium or hafnium can retard this omega process. The small size ($\leq 25$ angstroms) of the omega phase, however, can provide strengthening and hardening. Omega more readily forms in titanium alloys for molybdenum levels above about 8 weight percent.

The ability of the titanium alloy to age harden improves with a lower beta transus, thereby allowing for implants or devices with thicker cross sections to transform more completely to martensite upon cooling. The stronger beta stabilizing effect of molybdenum favors improved hardenability of the inventive alloy. This improved hardenability is beneficial for larger section knee and hip stem devices used in orthopaedics. That is, regions near the center of larger cross-section devices have an improved ability to be effectively quenched, and thus age-hardened, with improved hardenability. The titanium alloy including molybdenum above about 28 weight percent remains essentially a beta structure. With molybdenum between 9–11 weight percent, stress induced transformation of untransformed martensite can occur, and between 11–15 weight percent Mo, stress-induced twinning can occur.

Because of the advantages and limitations described above, the preferred inventive titanium alloy composition includes titanium with about between 2–30 weight percent molybdenum and with up to about 30 weight percent hafnium. However, hafnium in any amount sufficient to stabilize beta by producing a more sluggish transformation from beta is acceptable. Additionally, niobium can be substituted for molybdenum. At least one element selected from the group consisting of iron, chromium and silicon, each at levels of less than about 3 weight percent, can be optionally included in the composition for strengthening of the titanium alloy. Further, interstitial oxygen, nitrogen, or carbon can be increased for additional interstitial strengthening of the inventive alloy.

Table II provides a summary of mechanical test data and hardness data for selected Ti—Mo—Hf and Ti—Mo—Nb—Hf compositions described by the present invention. Both the as-quenched (from about 830° C.) and aged (6 hours, 500° C.) are given. Table II illustrates the unique combination of low modulus (12–17 msi), high strength (above 125 Ksi) and high hardness (above about 35 Rc) of the inventive alloy. Table II.

TABLE II

Tensile and Hardness Data

| Composition (wt. %) | Condition | UTS[1] (Ksi) | Y.S.[2] (Ksi) | Percent Elong. | % Red. Area | Rc[3] | Modulus (msi) |
|---|---|---|---|---|---|---|---|
| Ti—5Mo—7Hf | WQ[4] | 144 | 124 | 14.1 | 33.2 | 35(29)[5] | 15.9 |
| Ti—5Mo—7Hf | Aged | 150 | 130 | 15.6 | 54.9 | 37 | 16.2 |
| Ti—7Mo—7Hf | WQ | 136 | 100 | 7.8 | 10.5 | 45(26)[5] | 12.0 |
| Ti—7Mo—7Hf | Aged | 190 | 166 | 6.3 | 3.8 | 45 | 15.6 |
| Ti—9Mo—7Hf | WQ | 123 | 112 | 37.5 | 54.9 | 41(36)[5] | 16.3 |
| Ti—9Mo—7Hf | Aged | 191 | 179 | 6.3 | 8.9 | 42 | 16.6 |
| Ti—9Mo—9Hf | WQ | 119 | 106 | 43.8 | 62.4 | 36(40)[5] | 15.5 |
| Ti—9Mo—9Hf | Aged | 184 | 174 | 3.1 | 0.6 | 46 | 17.5 |
| Ti—7Mo—7Nb—1Fe | WQ | 150 | 150 | NA | 1.9 | 46(24)[5] | 16.4 |
| Ti—7Mo—7Nb—1Fe | Aged | 197 | 184 | 6.3 | 1.9 | 44 | 17.1 |
| Ti—5Mo—4Nb—7Hf | WQ | 137 | 96 | 17.2 | 18.1 | 44 | 11.8 |
| Ti—5Mo—4Nb—7Hf | Aged | 176 | 151 | 6.3 | 10.1 | 44 | 14.8 |
| Ti—7Mo—7Nb—7Hf | WQ | 114 | 90 | 40.6 | 59.4 | 36 | 14.7 |
| Ti—7Mo—7Nb—7Hf | Aged | 177 | 165 | 4.7 | 2.4 | 43 | 16.7 |
| Ti—6Mo—15Nb—6Hf | WQ | 105 | 83 | 45.8 | 57.8 | 29 | 14.5 |
| Ti—6Mo—15Nb—6Hf | Aged | 172 | 158 | 6.3 | 5.9 | 40 | 14.2 |

[1]UTS = Ultimate Tensile Strength
[2]Y.S. = Yield Strength
[3]Rc = Rockwell "C scale" hardness
[4]WQ = Water Quenched from about 830° C.
[5]( ) = Water Quenched from 900° C.

Table III shows comparison of selected compositions of the inventive alloy with other medical implant titanium alloys, Co—Cr—Mo, and 316 L stainless steel (S.S.).

TABLE III

New Ti—Mo—Hf Alloys Comparisons

| Material | Condition | U.T.S.[1] (Ksi) | Percent Elongation | Modulus | Rc[2] |
|---|---|---|---|---|---|
| 316 L S.S. | Annealed | 87 | 40 | 29 | 10 |
| 316 L S.S. | Cold Worked | 138 | 30 | 29 | 33 |
| Co Cr Mo | Cast | 115 | 8 | 31 | 44 |
| C.P. Ti | Grade 2 | 96 | 20 | 15.5 | 20's |
| Ti—6Al—4V | Annealed | 143 | 13 | 16.5 | 34 |
| Ti—6Al—4V | Forged | 160 | 8 | 16.5 | 34 |
| Ti—6Al—7Nb | Protasul 100 | 150 | 12 | 16 | 30's |
| TMZF ™ | Annealed | 155 | 20 | 13 | 30's |
| TMZF ™ | Aged | 173 | 3 | 15 | 42 |
| Ti—13Nb—13Zr | WQ[3] | 107 | 24 | 9.5 | 24 |
| Ti—13Nb—13Zr | Aged | 145 | 12 | 12 | 33 |
| Ti3510 | WQ | 82 | 18 | 10 | 30's |
| Ti3510 | Aged | 150 | 10 | 12 | 30's |
| Ti—7Mo—7Hf | WQ | 135 | 8 | 12 | 45 |
| Ti—7Mo—7Hf | Aged | 190 | 6 | 15.5 | 45 |
| Ti—15Nb—6Mo—6Hf | WQ | 105 | 45 | 14.5 | 29 |
| Ti—15Nb—6Mo—6Hf | Aged | 172 | 6 | 14 | 40 |
| Ti—7Mo—7Hf—1Fe | WQ | 150 | — | 16.5 | 46 |
| Ti—7Mo—7Hf—1Fe | Aged | 197 | 6 | 17 | 44 |
| Ti—9Mo—7Hf | WQ | 123 | 37 | 16 | 41 |
| Ti—9Mo—7Hf | Aged | 191 | 6 | 16.5 | 42 |
| Ti—5Mo—7Hf | WQ | 144 | 14 | 16 | 35 |
| Ti—5Mo—7Hf | Aged | 150 | 16 | 16 | 37 |
| Ti—11.5Mo—6Zr—4.5Sn | Beta III, Aged | 140–180 | 13–7 | 15 | 30's |
| Ti—3Al—8V—5Cr—4Mo—4Zr | Beta C, Annealed | 125 | 13 | 15 | 30's |
| Ti—3Al—8V—5Cr—4Mo—4Zr | Aged | 180 | 7 | 15.5 | 30's |

[1]UTS = Ultimate Tensile Strength
[2]Rc = Rockwell "C scale" hardness
[3]WQ = Water Quenched The inventive alloy is useful in the manufacture of a variety of medical implants and devices. The manufacture of medical devices from the inventive alloy includes cardiovascular devices such as vascular and other stents, percutaneous devices, vena cava filters, annuloplasty rings, vascular and other grafts, aneurysm clips and coils, heart valves, artificial hearts and ventricular assist devices, pacemakers and electrical signal carrying leads, power containers, sensors, and percutaneous devices. The manufacture of medical devices also includes implants such as orthopaedic implants, fracture plates, compression hip plates and screws, screws, staples and various internal and external tissue fixation devices, ENT devices, joint and surface replacements, and intramedullary rods. Similarly the inventive alloy is useful for neuro devices, bone graft substitute, dental implants and devices, orthodontic devices, various surgical instruments including cutting instruments, needles, guide and delivery wires and couplers, flexible catheters, and surgical cables. To improve biocompatibility of the medical implant or device made from the inventive alloy, at least a portion of the surface of the inventive alloy can be conversion surface hardened and/or coated. Such coatings can include, but are not limited to, antibiotics, pro- or anti-thrombogenic agents, anti-inflammatory agents, morphogenic proteins, morphogenic peptides, growth factors, or stem cells.

Selected examples of implants which can be made using the inventive Ti alloy are described below and include vascular stent devices. Additional medical devices manufactured from the inventive alloy include trauma plate and intramedullary rod devices, an orthopaedic hip replacement, a dental tooth replacement implant, and a pacemaker or defibrillator lead wire.

Certain aspects of the invention may be more readily understood with reference to the accompanying figures, all of which are not to scale but for illustrative purposes only.

Figure 1A:
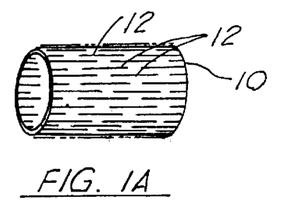
FIG. 1A is a schematic diagram of a self-expanding stent according to the invention, positioned within a segment of a blood vessel to be opened, in a first, non-deformed configuration.
Figure 1B:
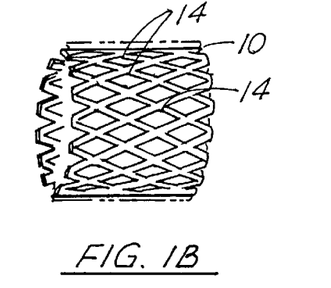
FIG. 1B is a perspective view illustrating the stent of FIG. 1A after expansion when released from the delivery catheter.

FIG. 1A shows an expandable stent 10 having a plurality of longitudinal slots 12 in a first, collapsed, non-expanded configuration. FIG. 1B is a perspective view illustrating the stent of FIG. 1A after expansion occurs following release within the vessel, creating a lattice-like structure of expanded material. In a case of a woven self-expanding stent construct, the expanded material forms a lattice created by the interconnection of the geometric wire centers 14.

Figure 2A:
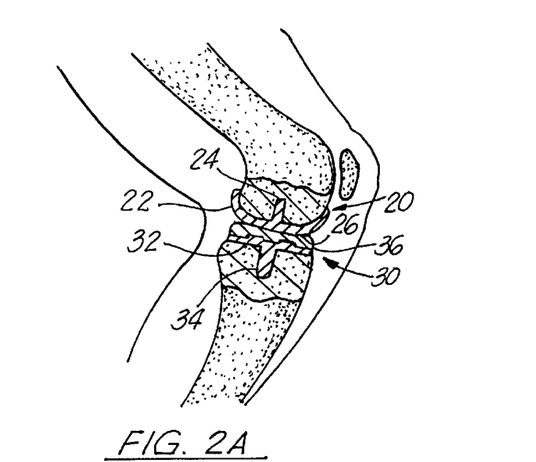
FIG. 2A is a schematic diagram of a knee joint prosthesis in place.
Figure 2B:
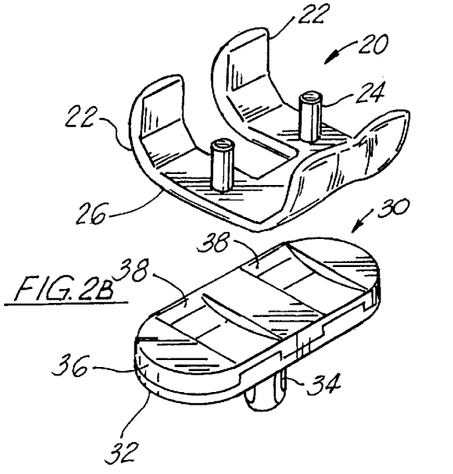
FIG. 2B is a schematic diagram of the parts of a typical knee joint.

A typical knee joint prosthesis fabricated from the inventive alloy is shown in situ in FIG. 2A as composed of the parts shown in FIG. 2B. The knee joint includes a femoral component 20 and a tibial component 30. The patella component is not shown. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibial platform 36, typically a polymer bearing material, is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform.

Figure 3A:
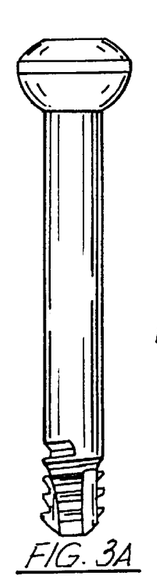
FIG. 3A is a schematic diagram of a typical screw for affixing bone plates.
Figure 3B:
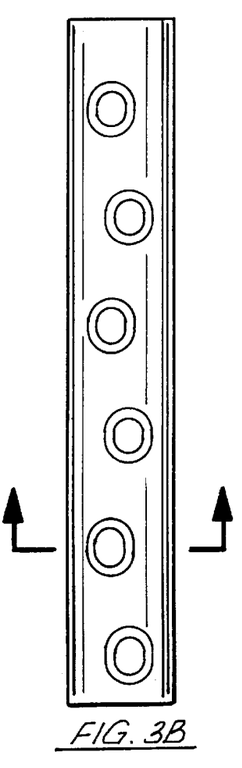
FIG. 3B is a diagram of a typical bone plate.
Figure 3C:
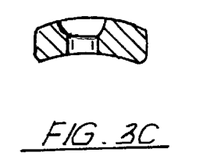
FIG. 3C is a cross-section of FIG. 3B taken along line 40.

FIG. 3A shows a typical bone screw manufactured from the inventive alloy. FIG. 3B shows a typical plate affixed by the screws. FIG. 3C is a cross-sectional view of the bone plate shown in FIG. 3B taken along line 40.

Figures 4A, 4B, 5, 6, 7A, 7B:
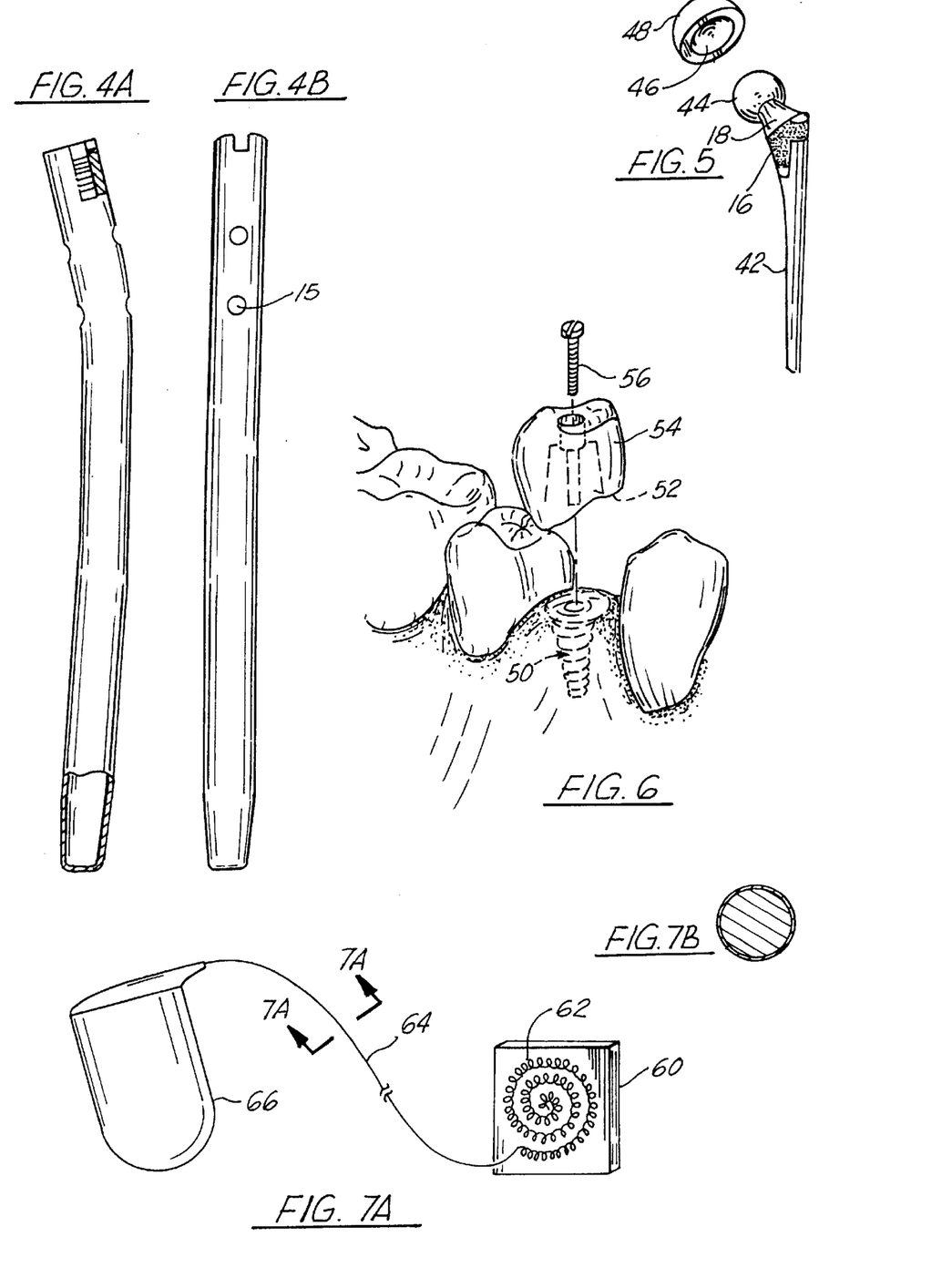
FIG. 4A is a schematic diagram of a side view of a typical intramedullary rod used in orthopedic applications.
FIG. 4B is a view of FIG. 4A rotated by 90°.
FIG. 5 is a schematic diagram showing components of a typical hip joint prosthesis.
FIG. 6 shows a partial cross section of a gum with a dental implant fabricated from the titanium alloy according to the present invention, wherein the root of the implant is implanted into the jawbone, an abutment of the inventive alloy projects above the gumline for receiving the crown, a porcelain veneer in tooth-shape attaches to an implant with an abutment screw, fabricated from the inventive alloy.
FIG. 7A is a schematic diagram of the components of a defibrillator, showing power source, lead wire, and polymeric patch with coiled electrode.
FIG. 7B is a cross-section of the lead wire of FIG. 7A.

FIG. 4A is a schematic diagram of a side view of a typical intramedullary rod used in orthopedic applications made from the invention titanium alloy. FIG. 4B is a view of the intramedullary rod shown in FIG. 4A rotated by 90°. Holes (15) in the rod are for receiving bone screws or lag screws.

A typical hip joint assembly fabricated from the invention alloy is shown is FIG. 5. The hip joint stem 42 fits into the femur while the femoral head 44 of the prosthesis fits into and articulates against the inner polymer lining 46 of an acetabular cup 48 which in turn is affixed to the pelvis (not shown). A porous metal bead or wire mesh coating 16 may be incorporated to allow stabilization of the implant by ingrowth of surrounding tissue into the porous coating. Similarly, such a coating can also be applied to the acetabular component. The femoral head 44 may be an integral part of the hip joint stem 42 or may be a separate component mounted upon a conical taper at the end of the neck 18 of the hip joint prosthesis.

FIG. 6 shows a fixture 50 of the inventive alloy implanted into a jaw bone. The fixture 50 is capped with an abutment 52 of the invention alloy for receiving a crown 54. In a typical implantation procedure, assuming that the original tooth has been removed, an incision is made into the gum above the implant site. The site is prepared by peeling back gum tissue and drilling into the jaw bone. A fixture is then screwed or pressed into place in the jaw bone and the site is covered from about 3 to about 6 months to allow bone to grow around the implant and stabilize it in the jaw bone. After this period, the top of the fixture 50 is exposed and an abutment 52 is attached to the fixture. A crown 54, having a socket corresponding to the abutment, is then anchored to the abutment using an abutment screw 56, of the inventive alloy to complete the method of implantation. The fixture 50 is prepared from the inventive alloy. The abutment 52 and any screws 56 are also fabricated from the inventive alloy. The crown 54 is fabricated to include an abutment made from the inventive alloy, that is suitably coated to provide the appearance of a natural tooth.

FIG. 7A shows a defibrillator including a flexible silicone polymeric patch 60 with a coil of conductive wire 62 (typically titanium, stainless steel, or cobalt-nickel-chromium) on the side of the silicone patch 60 that will contact muscle tissue. When in place in the body, the lead wire 64 that carries power to the coil 62 may extend out of the body (through the skin) and is electrically connected to a power source in a protective container 66. According to the invention, the lead wire 64 is fabricated with the invention titanium alloy. FIG. 7B is a cross-section of the lead wire 64. The power source 60, if implanted, can also be contained in a shell of the invention alloy.

Although the present invention has been described with reference to its preferred embodiments, those skilled in the arts will recognize changes that may be made in form and structure which do not depart from the spirit of the invention already described in the specification and embodied in the claims which follow.

What is claimed is:

1. A medical implant or device fabricated from a titanium alloy suitable for use in the fabrication of medical implants and devices, said medical implant or device comprising:
   components at least partially fabricated from a metal alloy comprising:
   a) titanium;
   b) between about 6 to 9 weight percent molybdenum;
   c) between about 6 to 9 weight percent hafnium;
   wherein the alloy provides for high-strength and hardness, low elastic modulus, enhanced corrosion resistance, and surface hardening of the medical implant or device.

2. A medical implant or device of claim 1, wherein the alloy further includes up to about 3 weight percent of at least one element selected from the group consisting of iron, chromium and silicon.

3. A medical implant or device of claim 1, wherein additional interstitial strengthening of the alloy is achieved by increased levels of an element selected from the group consisting of oxygen, nitrogen and carbon.

4. A medical implant or device of claim 1, wherein the alloy composition is titanium, about 7 weight percent molybdenum and about 7 weight percent hafnium.

5. A medical implant or device of claim 1, wherein at least a portion of said implant or device is surface hardened by a process selected from the group consisting of oxidation and nitriding to form a hard, diffusion bonded, conversion surface oxide or nitride.

6. The medical implant or device of claim 1, wherein at least a portion of said implant or device is surface hardened by a process selected from the group consisting of oxygen diffusion hardening and nitrogen diffusion hardening, leaving a metallic-type appearance.

7. The medical implant or device of claims 1, 5 or 6, wherein at least a portion of a surface of the implant or device is coated with a low friction coating.

8. The medical implant or device of claims 1, 5 or 6, wherein at least a portion of a surface of the implant or device is coated with an agent to improve hemocompatibility, soft tissue attachment, or bone attachment, said agent selected from the group consisting of antibiotics, anti-thrombogenics, pro-thrombogenics, anti-inflammatories, morphogenic proteins, peptides, growth factors, and stem cells.

9. The medical implant or device of claim 1, wherein the alloy is hot or cold mechanically worked in order to optimize the grain size, strength, low elastic modulus, and toughness of the alloy.

10. A medical implant or device fabricated from a titanium alloy suitable for use in the fabrication of medical implants and devices, said medical implant or device comprising:
    components at least partially fabricated from a metal alloy comprising:
    a) titanium;
    b) 2 weight percent molybdenum;
    c) 6 weight percent hafnium;
    d) 10 weight percent niobium;
    wherein the alloy provides for enhanced strength and hardness, low modulus, corrosion resistance and surface hardening of the medical implant or device.

11. The medical implant or device of claim 10, wherein the alloy further includes up to about 3 weight percent of at least one element selected from the group consisting of iron, chromium, and silicon.

12. The medical implant or device of claim 10, wherein additional interstitial strengthening of the alloy is achieved by an increase in the level of an element selected from the group consisting of oxygen, nitrogen and carbon.

13. The medical implant or device of claim 10, wherein at least a portion of said implant or device is surface hardened by a process selected from the group consisting of oxidation and nitriding to form a hard, diffusion bonded, conversion surface oxide or nitride.

14. The medical implant or device of claims 10, 12 or 13, wherein at least a portion of said implant or device is surface hardened by a process selected from the group consisting of oxygen diffusion hardening and nitrogen diffusion hardening leaving a metallic-type appearance.

15. The medical implant or device of claim 10, wherein at least a portion of a surface of the implant or device is coated with a low friction coating.

16. The medical implant or device of claim 10, wherein at least a portion of a surface of the implant or device is coated to improve hemocompatibility, soft tissue attachment, or bone attachment with an agent selected from the group consisting of antibiotics, anti-thrombogenic agents, pro-thrombogenic agents, anti-inflammatory agents, morphogenic proteins, peptides, growth factors, and stem cells.

17. The medical implant or device of claim 10, wherein the alloy is hot or cold mechanically worked in order to optimize the grain size, strength, low elastic modulus, and toughness of the alloy.

18. A titanium alloy suitable for use in non-medical device applications comprising;
   components at least partially fabricated from a metal alloy comprising:
   a) titanium;
   b) between about 6 to 9 weight percent molybdenum;
   c) between about 6 to 9 weight percent hafnium;
   wherein the alloy provides for high-strength and hardness, low elastic modulus, enhanced corrosion resistance, and surface hardening.

19. A titanium alloy suitable for use in non-medical device applications comprising;
   components at least partially fabricated from a metal alloy comprising:
   a) titanium;
   b) 2 weight percent molybdenum;
   c) 6 weight percent hafnium;
   d) 10 weight percent niobium;
   wherein the alloy provides for enhanced strength and hardness, low modulus, corrosion resistance and surface hardening.

20. The titanium alloy of claim 19, wherein the alloy further includes up to about 3 weight percent of at least one element selected from the group consisting of iron, chromium and silicon.

* * * * *